United States Patent [19]

Kato et al.

[11] Patent Number: 5,180,728
[45] Date of Patent: Jan. 19, 1993

[54] PYRIMIDOINDOLE DERIVATIVES AND PROCESSES FOR PREPARATION THEREOF

[75] Inventors: Masayuki Kato, Kyoto; Shigetaka Nishino, Osaka; Kiyotaka Ito, Ikeda; Hisashi Takasugi, Osaka, all of Japan

[73] Assignee: Fujisawa Pharmaceutical Company, Ltd., Osaka, Japan

[21] Appl. No.: 572,247

[22] Filed: Aug. 27, 1990

[30] Foreign Application Priority Data

Sep. 25, 1989 [GB] United Kingdom ............... 8921634
Jul. 30, 1990 [GB] United Kingdom ............... 9016704

[51] Int. Cl.$^5$ .................. A61K 31/505; C07D 403/06
[52] U.S. Cl. ..................... 514/267; 544/252; 548/491; 548/492; 548/493; 548/505; 548/507; 548/509; 548/313.7; 548/312.1; 548/333.5; 548/335.5; 548/343.1
[58] Field of Search .................... 544/252; 514/267

[56] References Cited

U.S. PATENT DOCUMENTS

| | | |
|---|---|---|
| 4,409,224 | 10/1983 | Jirkovsky ............... 544/252 |
| 4,695,578 | 9/1987 | Coates et al. ........... 548/336 |
| 5,034,398 | 7/1991 | King ..................... 546/112 |

FOREIGN PATENT DOCUMENTS

| | | |
|---|---|---|
| 254584 | 1/1988 | European Pat. Off. . |
| 266899 | 5/1988 | European Pat. Off. . |
| 276559 | 8/1988 | European Pat. Off. . |
| 0306323 | 3/1989 | European Pat. Off. . |

OTHER PUBLICATIONS

*IUPAC, Nomenclature of Organic Chemistry*, pp. 31, 76, 258 (1979).
Goodman and Gilman's *The Pharmacological Basis of Therapeutics* (7th Ed.), pp. 633–634 (1985).

Primary Examiner—Mukund J. Shah
Assistant Examiner—E. Bernhardt
Attorney, Agent, or Firm—Oblon, Spivak, McClelland, Maier & Neustadt

[57] ABSTRACT

A compound of the formula:

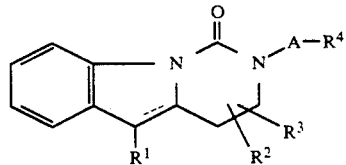

wherein $R^1$, $R^2$ and $R^3$ are each hydrogen, lower alkyl, lower alkenyl, aryl or ar(lower)alkyl, $R^4$ is imidazolyl, which may have alkyl or imino-protective group as substituents, or pyridyl, A is lower alkylene, and ╌╌╌ is single bond or double bond, and pharmaceutically acceptable salts thereof, having 5-HT antagonism.

9 Claims, No Drawings

PYRIMIDOINDOLE DERIVATIVES AND PROCESSES FOR PREPARATION THEREOF

The present invention relates to novel pyrimidoindole derivatives and a pharmaceutically acceptable salt thereof. More particularly, it relates to novel pyrimidoindole derivatives and a pharmaceutically acceptable salt thereof which have pharmacological activities such as 5-hydroxytryptamine (5-HT) antagonism and the like, to processes for preparation thereof, to a pharmaceutical composition comprising the same and to a use of the same as a medicament.

Accordingly, one object of the present invention is to provide novel pyrimidoindole derivatives and a pharmaceutically acceptable salt thereof, which are useful as a potent and selective antagonist of 5-HT receptor.

Another object of the present invention is to provide processes for preparation of said pyrimidoindole derivatives or a salt thereof.

A further object of the present invention is to provide a pharmaceutical composition comprising, as an active ingredient, said pyrimidoindole derivatives or a pharmaceutically acceptable salt thereof.

Still further object of the present invention is to provide a use of said pyrimidoindole derivatives or a pharmaceutically acceptable salt thereof as a 5-HT antagonist useful for treating or preventing 5-hydroxytryptamine mediated diseases, for example, central nervous system (CNS) disorders such as psychosis (e.g. schizophrenia, mania, etc.), anxiety, and depression; pains or aches such as headaches (e.g. migraine, cluster headaches, vascular headaches, etc.) and neuralgia (e.g. trigeminal neuralgia, etc.); gastrointestinal disorders such as symptoms of gastrointestinal dysfunction such as occur with, for example, dyspepsia, peptic ulcer, reflux oesophagitis and flatulence, and irritable bowel syndrome (IBS); nausea or vomiting, each of which may h=associated with cancer therapy; motion sickness; and the like in human being or animals, particularly nausea and vomiting.

With regard to the states of the arts in this field, for example, the following compound is known.

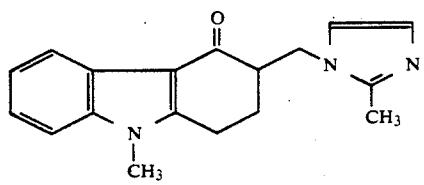

(Japanese Patent Gazette KOKAI 60-214784)

As a result of an extensive study, the inventors of the present invention could obtain the pyrimidoindole derivatives which have strong pharmacological activities.

The pyrimidoindole derivatives of the present invention are novel and can be represented by the formula (I)
:

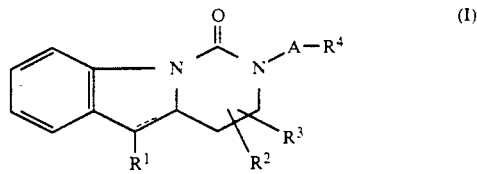

wherein $R^1$, $R^2$, and $R^3$ are each hydrogen, lower alkyl, lower alkenyl, aryl or ar(lower)alkyl,
$R^4$ is imidazolyl which may have suitable substituent(s) or pyridyl,
A is lower alkylene, and
⋯ is single bond or double bond.

With regard to the compound (I) of the present invention, it is to be noted that there may be one or more optically isomeric pairs due to the presence of one or more asymmetric carbon atom(s) and these isomers or a mixture thereof are included within a scope of the compound (I) of the present invention.

According to the present invention, the object compound (I) can be prepared by the following processes.

Process 1

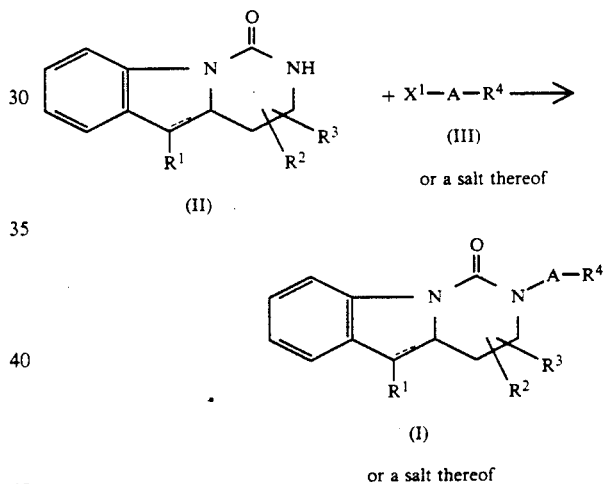

Process 2

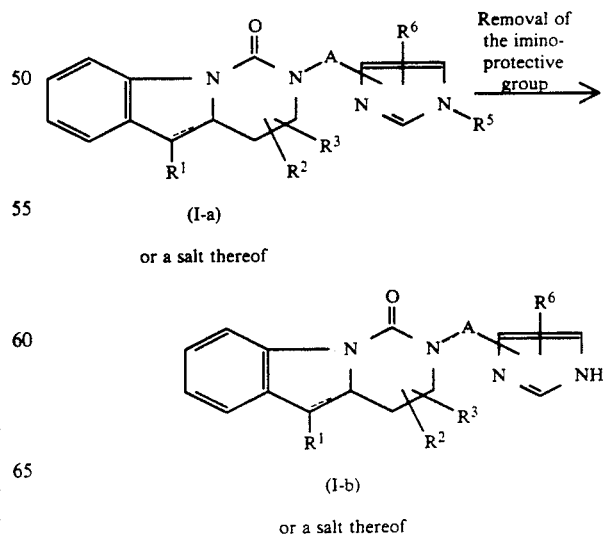

Process 3

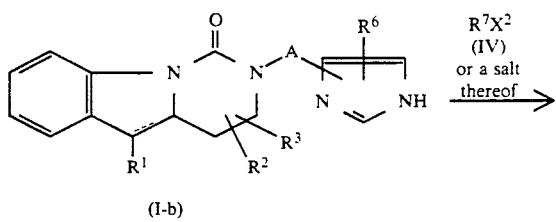

(I-b)

or a salt thereof

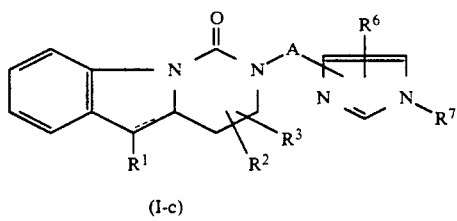

(I-c)

or a salt thereof

Process 4

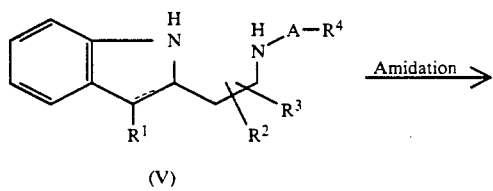

(V)

↓ Amidation (I)

or a salt thereof wherein $R^1$, $R^2$, $R^3$, $R^4$, A and ⋯ are each as defined above, $R^5$ is imino-protective group,
$R^6$ is hydrogen or lower alkyl,
$R^7$ is lower alkyl, and
$X^1$ and $X^2$ are each acid residue.

Suitable salt of the compounds (I), (I-a), (I-b), (I-c), (III), (IV) and (V) are conventional non-toxic, pharmaceutically acceptable salt and may include a salt with a base or an acid addition salt such as a salt with an inorganic base, for example, an alkali metal salt (e.g. sodium salt, potassium salt, cesium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.), etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); and the like, and the preferable example thereof is an acid addition salt.

In the above and subsequent descriptions of the present specification, suitable examples and illustrations of the various definitions which the present invention include within the scope thereof are explained in detail as follows.

The term "lower" is intended to mean 1 to 6 carbon atoms, preferably 1 to 4 carbon atoms, unless otherwise indicated.

Suitable "lower alkyl" may include straight or branched one, having 1 to 6 carbon atom(s), such as methyl, ethyl, propyl, isopropyl, butyl, t-butyl, pentyl, hexyl, preferably one having 1 to 4 carbon atoms, and the like, in which the most preferred one is methyl, ethyl or propyl.

Suitable "lower alkenyl" may include vinyl, 1-propenyl, allyl, 1-butenyl, 2-butenyl, 2-pentenyl, and the like, preferably one having 2 to 4 carbon atoms, in which the most preferred one is allyl.

Suitable "aryl" may include phenyl, tolyl, xylyl, mesityl, cumenyl, naphthyl, and the like, in which the preferred one is $C_6$–$C_{10}$ aryl and the most preferred one is phenyl.

Suitable "ar(lower)alkyl" may include mono-[or di- or tri-)phenyl(lower)alkyl such as trityl, benzhydryl, benzyl, phenethyl, and the like, in which the preferred one is $C_6$–$C_{10}$ ar($C_1$–$C_6$)alkyl and the most preferred one is benzyl.

Suitable "imidazolyl" means 1H-imidazolyl-1-yl, 1H-imidazol-2-yl, 1H-imidazol-4-yl and 1H-imidazol-5-yl.

Suitable substituent in the terms "imidazolyl which may have suitable substituent(s)" is conventional one used in a pharmaceutical field and may include lower alkyl as mentioned above, imino-protective group as mentioned below, and the like.

Suitable "pyridyl" means 2-pyridyl, 3-pyridyl and 4-pyridyl.

Suitable "imino-protective group" may include conventional one, and the preferable example thereof is ar(lower)alkyl such as mono-(or di- or tri-)phenyl-(lower)alkyl (e.g. benzyl, benzhydryl, trityl, etc.), acyl such as N,N-di(lower)alkylsulfamoyl (e.g. N,N-dimethylsulfamoyl, etc.), lower alkanesulfonyl (e.g. mesyl, etc.), arenesulfonyl (e.g. tosyl, etc.), and the like, in which the most preferred one is trityl, benzyl or N,N-dimethylsulfamoyl.

Suitable "lower alkylene" may include straight or branched one, having 1 to 6 carbon atom(s), such as methylene, methylmethylene, ethylene, trimethylene, propylene, tetramethylene, and the like, in which the most preferred one is methylmethylene.

Suitable "acid residue" may include halogen as fluoro, chloro, bromo and iodo, and the like.

Particularly, the preferred embodiments of $R^1$, $R^2$, $R^3$, $R^4$, A and ⋯ are as follows.

$R^1$ is hydrogen; lower alkyl (e.g. methyl, ethyl, isopropyl, etc.); lower alkenyl (e.g. allyl, etc.); aryl (e.g. phenyl, etc.); or ar(lower)alkyl such as mono- or di- or triphenyl(lower)alkyl (e.g. benzyl, etc.);

$R^2$ is hydrogen; or lower alkyl (e.g. methyl, etc.);

$R^3$ is hydrogen; or lower alkyl (e.g. methyl, etc.);

$R^4$ is imidazolyl which may have one to three substituent(s) selected from the group consisting of lower alkyl and imino-protective group, for example, 1H-imidazol-4-yl, 5-lower alkyl-1H-imidazol-4-yl (e.g. 5-methyl-1H-imidazol-4-yl, 5-ethyl-1H- imidazol-4-yl, etc.), 1-ar(lower)alkyl-5-lower alkyl-1H-imidazol-4-yl such as 1- mono- or di- or triphenyl(lower)alkyl-5-lower alkyl-1H-imidazol-4-yl (e.g. 1-trityl-5-methyl-1H-imidazol-4-yl, 1-trityl-5-ethyl-1H-imidazol-4-yl, etc.), 1-ar(lower)alkyl-1H-imidazol-4-yl such as 1-mono- or di- or triphenyl(lower)alkyl-1H-imidazol-4-yl (e.g. 1-trityl-1H-imidazol-4-yl, etc.), 1-lower alkyl-5-lower alkyl-1H-imidazol-4-yl (e.g. 1-methyl-5-methyl-1H-imidazol-4-yl, etc.); pyridyl (e.g. 4-pyridyl, etc.);

A is lower alkylene (e.g. methylene, methylmethylene, etc.); and

······ is single bond or double bond.

The processes 1 to 4 for preparing the object compound (I) of the present invention are explained in detail in the following.

Process 1

The object compound (I) or a salt thereof can be prepared by reacting the compound (II) with the compound (III) or a salt thereof.

The present reaction is usually carried out in the present of a base such as alkyl lithium (e.g. n-butyllithium, etc.), alkali metal hydride e.g. sodium hydride, potassium hydride, etc.), and the like.

The present reaction is usually carried out in a solvent such as dioxane, dimethylsulfoxide, dimethylformamide, diethylformamide, dimethylacetamide, benzene, hexane, tetrahydrofuran, or any other solvent which does not adversely affect the reaction.

The reaction temperature is not critical and the reaction is usually carried out under cooling, at ambient temperature or under heating.

Process 2

The object compound (I-b) or a salt thereof can be prepared by subjecting the compound (I-a) or a salt thereof to removal reaction of the imino-protective group.

Suitable method for this removal may include conventional one such as hydrolysis, reduction, or the like. The hydrolysis is preferably carried out in the presence of the base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate, (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-one, 1,4-diazabicyclo[2,2,2]-octane, 1,5-diazabicyclo[5,4,0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and the reaction is usually carried out at ambient temperature or under warming or heating.

Process 3

The object compound (I-c) or a salt thereof can be prepared by reacting the compound (I-b) or a salt thereof with the compound (IV) or a salt thereof.

The present reaction is usually carried out in the presence of a base such as alkyl lithium (e.g n-butyl lithium, etc.), alkali metal hydride (e.g. sodium hydride, potassium hydride, etc.), di(lower)alkylamine (e.g. diisopropylamine, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

Process 4

The object compound (I) or a salt thereof can be prepared by subjecting the compound (V) to amidation reaction.

The present reaction is carried out in the presence of a conventional condensing agent such as N,N'-carbonyldiimidazole, and the like.

The present reaction is usually carried out in the presence of a base such as 1,8-diazabicyclo[5.4.0]-7-undecene and ones explained in Process 2.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

The reaction temperature is not critical and the reaction is usually carried out under cooling, at ambient temperature or under heating.

Among the starting compounds (II), (III), (IV) and (V), some of them are new and such compounds can be prepared by the methods of Preparations mentioned below.

The object compound (I) of the present invention can be isolated and purified in a conventional manner, for example, extraction, precipitation, fractional crystallization, recrystallization, chromatography, and the like.

The object compound (I) thus obtained can h=converted to its salt by a conventional method.

The optically active isomers of the object compound (I) can be resolved by a conventional method such as a resolution by reacting a mixture of isomers with an optically active reagent. Such reagents include optically active acids e.g., benzyloxycarbonyl-L-phenylalanine, di-p-toluoyltartaric acid, etc.) or acid derivatives such as acid chloride (e.g., l-menthoxyacetyl chloride, etc.) or acid anhydride and the like.

The object compound (I) of the present invention are novel and exhibit pharmacological activities such as 5-HT antagonism, especially, 5-$HT_3$ antagonism, and the like and therefore are useful as 5-HT antagonist for treating or preventing 5-hydroxytryptamine mediated diseares, for example, central nervous system (CNS) disorders such as psychosis (e.g. schizophrenia, mania, etc.) anxiety, and depression; pains or aches such as headaches (e.g. migraine, cluster headaches, vascular headaches, etc.), and neuralgia (e.g. trigeminal neuralgia, etc.); gastrointestinal disorders such as symptom of gastrointestinal dysfunction such as occur with, for example, dyspepsia, peptic ulcer, reflux oesophagitis and flatulence, and irritable bowel syndrome (IBS); nausea or vomiting, each of which may be associated with cancer therapy; motion sickness; and the like.

Further, it is expected that the object compound (I) of the present invention are useful as therapeutical and/or preventive agents for obesity; lung embolism; arrhythmia; withdrawal syndrome resulting from addition to a drug or substance of abuse; stress-related psychiatric disorders; rhinitis; and serotonin-induced nasal disorders, and the like.

In order to illustrate the usefulness of the object compounds (I), pharmacological activity of representative compound of the present invention are shown below.

TEST COMPOUND (1) 3,4-Dihydro-5-methyl-2-[(5-methyl-1H-imidazol-4-yl-methyl]pyrimido[1,6-a]indol-1(2H)-one hydrochloride (hereinafter referred to as Compound   )
(2) 3,4-Dihydro-5-methyl-2-[1-(5-methyl-1H-imidazol-4-yl)ethyl]pyrimido[1,6-a]indol-1(2H)-one hydrochloride hereinafter referred to as Compound   )

TEST

Inhibition of Bezold-Jarisch reflux Test Method

Male Sprague-Dawley rats weighing 260–350 g were anesthetized intraperitoneally with 1.25 g/kg urethane.

Blood pressure and heart rate were monitored continuously from the left common carotid artery with a pressure transducer. A right femoral vein was connulated for the intravenous injection (iv) of drugs. The trachea was also connulated to ease the respiration.

Rats were given a rapid bolus injection of 2-methyl-5-hydroxytryptamine (32 μg/kg, iv) to establish the control bradycardic response. Once the heart rate returned to base line, the rats were given the test compound (iv), followed by 5-minutes interval and another bolus injection of 2-methyl-5-hydroxytryptamine (32 μg/kg., iv).

| Test Results: | |
|---|---|
| Compound | $ED_{50}$ (μg/kg) |
| ① | 0.56 |
| ② | 1.5 |

For therapeutic or preventive administration, the object compound (I) of the present invention are used in the form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary from and also depend upon the age, conditions of the patient, a kind of diseases or conditions, a kind of the compound (I) to be applied, etc. In general amounts between 0.01 mg and about 500 mg or even more per day may be administered to a patient. An average single dose of about 0.05 mg, 0.1 mg, 0.25 mg, 0.5 mg, 1 mg, 20 mg, 50 mg, 100 mg of the object compound (I) of the present invention may be used in treating diseases.

The following Preparations and Examples are given for the purpose of illustrating the present invention.

Preparation 1

To a solution of 2-(3-methylindol-2-yl)ethylamine (1.74 g) in tetrahydrofuran (200 ml) at room temperature was added 1,1'-carbonyldiimidazole (1.6 g) in small portions. After one hour of stirring, the reaction mixture was evaporated in vacuo. The residue was dissolved in toluene and the solution was evaporated in vacuo. The oil obtained was heated at 100° C. for 40 minutes and then cooled. Purification of the residue with silica gel column chromatography (chloroform) gave 3,4-dihydro-5-methylpyrimido[1,6-a]indol-1(2H)-one (0.8 g).

mp : 185°–189° C. .

IR (Nujol) : 3200, 3100, 1685, 1620, 1335 cm$^{-1}$

NMR (CDCl$_3$, δ) : 2.20 (3H, s), 3.03 (2H, t, J=6Hz), 3.53 (2H, dt, J=2.5, 6Hz), 5.86 (1H, s), 7.29 (2H, m), 7.46 (1H, m), 8.31 (1H, d, J=6Hz).

Preparation 2

3,4-Dihydropyrimido[1,6-a]indol-1(2H)-one was prepared in a similar manner to that of Preparation 1.

mp : 197°–199° C.

IR (Nujol) : 3200, 1690, 1675, 1600 cm$^{-1}$.

NMR (CDCl$_3$, δ) : 3.10 (2H, t, J=5.86Hz), 3.5–3.6 (2H, m), 6.20 (1H, br s), 6.33 (1H, s), 7.0–7.3 (2H, m), 7.49 (1H, dd, J=2.06Hz, 6.96Hz), 8.32 (1H, dd, J=1.17Hz, 8.75Hz).

MS (m/e) : 186 (M+).

Preparation 3

To a solution of 2-(3-methylindol-2-yl)ethylamine (2.5 g) in acetic acid [25 ml] at 15° C. was added sodium cyanoborohydride (1.62 g) in one portion. The solution was stirred at room temperature. After 3 hours, sodium cyanoborohydride (1.0 g) was added and the mixture was stirred at room temperature for 12 hours. After dilution with ice-water, the reaction mixture was made basic with sodium hydroxide pellets and extracted three times with ether. The ether layer was washed with water and brine, dried over anhydrous sodium sulfate, and evaporated in vacuo to give 2-(2,3-dihydro-3-methylindol-2-yl)ethylamine (1.80 g) as an oil. The oil was used in the next reaction without further purification.

IR (Film) : 3300, 1605, 1240 cm$^{-1}$.

Preparation 4

To a solution of crude 2-(2,3-dihydro-3-methylindol-2-yl)ethylamine (1.75 g) in tetrahydrofuran 12 ml) at room temperature was added in small portions 1,1'-carbonyldiimidazole (1.1 g). After being stirred for hours, the reaction mixture was evaporated in vacuo. The oil obtained was dissolved in toluene (25 ml) and the solution was heated at 110° C. for 1.5 hours. After evaporation of the solvent, the residue was purified by silica gel column chromatography (1% methanol-chloroform) to give crystals. Recrystallization from chloroform-ethyl acetate-hexane gave 3,4,4a,5-tetrahydro-5-methylpyrimido-[1,6-a]indol-1(2H)-one (0.65 g).

mp: 204°-207° C.

IR (Nujol) : 3180, 1670, 1595, 1300 cm$^{-1}$.

NMR (DMSO-d$_6$, δ) : 1.34 (3H, d, J=7Hz), 1.80 (1H, m), 2.26 (1H, m), 3.03-3.30 (3H, m), 3.71 (1H, dt, J=3, 11Hz), 6.68 (1H, br s), 6.87 (1H, t, J=7Hz), 7.00-7.20 (2H, m), 7.71 (1H, d, J=7Hz).

Preparation 5

To a solution of diisopropylamine (809 mg) in tetrahydrofuran (20 ml) at −30° C. under nitrogen atmosphere was added 1.64M butyllithium in hexane (5.33 ml). After being stirred at the same temperature for 30 minutes, the mixture was treated with a solution of indol-2-yl-acetonitrile (1.25 g) in tetrahydrofuran (10 ml) at −60° C. over 15 minutes. The mixture was stirred at the same temperature for an hour, and a solution of methyl iodide (1.14 g) in tetrahydrofuran (10 ml) was added dropwise over an hour. After the mixture was stirred at -60° C. for one hour and at ambient temperature for 2 hours, it was diluted with chilled water, and extracted two times with ethyl acetate. The organic layer was washed with brine, dried over magnesium sulfate, and evaporated in vacuo. The residue was purified by alumina column chromatography (10% ethylacetate-toluene) to give 2-(indol-2-yl)-2-methylpropiononitrile (354 mg).

mp : 76°-78° C.

IR (Nujol) : 3250, 2240, 1660, 1615 cm$^{-1}$.

NMR (CDCl$_3$, δ) : 1.81 (6H, s), 6.4-6.5 (1H, m), 7.0-7.6 (4H, m), 8.34 (1H, s).

MS (m/e) : 184 (M$^+$).

Preparation 6

The solution of methyl 2-oxo-5-hexenoate (19.5 g), phenylhydrazine (14.8 g) and anhydrous p-toluenesulfonic acid (0.5 g) in dry benzene was refluxed for 0.5 hour. The solution of anhydrous p-toluenesulfonic acid (35.3 g) in dry-benzene (150 ml) was added to the solution at 50° C. over five minutes. After being stirred at 50°-60° C. for 1 hour, the mixture was refluxed for 2 hours. After cooling, the reaction mixture was diluted with chilled water and extracted twice with ethyl acetate. The organic layer was washed with water and brine, dried over anhydrous magnesium sulfate, and evaporated in vacuo. The residue was purified by silica gel column chromatography (10% ethyl acetate-toluene) to give 3-allyl-2-indolecarboxylic acid methyl ester (13.6 g) as crystals.

mp 79°-82° C.

IR (Nujol) : 3320, 1680 cm$^{-1}$.

NMR (DMSO-d$_6$, δ) : 3.84 (2H, d, J=6.33Hz), 3.88 (3H, s), 4.9-5.2 (2H, m), 5.8-6.1 (1H, m), 7.0-7.3 (2H, m), 7.43 (1H, d, J=8.24Hz), 7.66 (1H, d, J=7.95Hz), 11.63 (1H, s).

Preparation 7

The following compounds were prepared in a similar manner to that of Preparation 6.

(1) 3-Ethyl-2-indolecarboxylic acid methyl ester mp : 114°-116° C.

IR (Nujol) : 3310, 1670, 1530 cm$^{-1}$.

NMR (DMSO-d$_6$, δ) : 1.21 (3H, t, J=7.41Hz) 3.07 (2H, q, J=7.41Hz), 3.89 (3H, s), 7.0-7.8 (4H, m), 11.54 (1H, s).

(2) 3-Isopropyl-2-indolecarboxylic acid methyl ester mp 82°-85° C.

IR (Nujol) : 3330, 1670, 1530 cm$^{-1}$.

NMR (DMSO-d$_6$, δ) : 1.40 (6H, d, J=7.10Hz), 3.88 (3H, s), 3.9-4.3 (1H, m), 6.9-7.9 (4H, m), 11.48 (1H, s).

Preparation 8

The mixture of 3-allyl-2-indolecarboxylic acid methyl ester (13.1 g) and lithium borohydride (2.65 g) in tetrahydrofuran (100 ml) was refluxed for 3 hours. After cooling, the reaction mixture was diluted with chilled water, made acidic with 2N-hydrochloric acid. The mixture was neutralized with aqueous sodium bicarbonate solution and extracted twice with ethyl acetate. The organic layer was washed with brine, dried over anhydrous magnesium sulfate, and evaporated in vacuo to give 3-allyl-2-hydroxymethylindole (11.2 g) as an oil. The oil was used in the next reaction without further purification.

IR (Film) : 3400, 1700, 1630 cm$^{-1}$.

NMR (CDCl$_3$, δ) : 3.50 (2H, d, J=6.04Hz), 4.80 (1H, s), 4.9-5.2 (2H, m), 5.9-6.2 (1H, m), 7.0-7.6 (4H, m), 8.20 (1H, s).

Preparation 9

To the suspension of lithium aluminum hydride (4.15 g) in tetrahydrofuran (41 ml) at 15°-30° C. under a nitrogen atmosphere was added dropwise over 45 minutes 3-ethyl-2-indolecarboxylic acid methyl ester (22.2 g) in tetrahydrofuran. After the mixture was stirred at room temperature for an hour, ethyl acetate (200 ml) was added dropwise at 20°-30° C., followed by the addition of methanol (10 ml) at the same temperature. The reaction mixture was treated with saturated aqueous potassium sodium tartrate solution (150 ml). Separated organic layer was dried over anhydrous magnesium sulfate and evaporated in vacuo. The residue was purified by silica gel column chromatography (10% ethylacetate-n-hexane) to give 3-ethyl-2-hydroxymethylindole (14.0 g) as crystals.

mp 160°-161° C.

IR (Nujol) : 3350, 1600 cm$^{-1}$.

Preparation 10

The following compound was prepared in a similar manner to that of Preparation 8.

3-Benzyl-2-hydroxymethylindole mp : 100°-106° C.

IR (Nujol) : 3400, 1600 cm$^{-1}$.

NMR (CDCl$_3$, δ) : 4.04 (2H, s), 4.63 (2H, s), 6.9-7.5 (9H, m), 8.3 (1H, s).

Preparation 11

The following compound was prepared in a similar manner to that of Preparation 9.

3-Isopropyl-2-hydroxymethylindole mp : 102°-103° C.

IR (Nujol) : 3400, 1615 cm$^{-1}$.

NMR (CDCl$_3$, δ) : 1.39 (6H, d, J=7.0Hz), 3.0-3.3 (1H, m), 4.69 (2H, s), 7.0-7.3 (3H, m), 7.6-7.8 (1H, m), 8.18 (1H, s).

Preparation 12

The mixture of 3-isopropyl-2-hydroxymethylindole (29 g) and manganese dioxide (66.7 g) in ethyl acetate (435 ml) was reflux for 2 hours. After filtration of the insoluble materials, the filtrate was evaporated in vacuo. The residue was purified by silica gel column chromatography (10% ethyl acetate-toluene) to give 3-isopropyl-2-indolecarbaldehyde (24.2 g) as crystals.

mp : 63°–65° C. .

IR (Nujol) : 3300, 3150, 1645, 1620, 1610 cm$^{-1}$

NMR (DMSO-d$_6$, δ) : 1.47 (6H, d, J=7.04Hz), 3.7–3.9 (1H, m), 7.0–7.1 (1H, m), 7.2–7.4 (1H, m), 7.44 (1H, d, J=8.3Hz), 7.86 (1H, d, J=8.14Hz), 10.12 (1H, s), 11.60 (1H, s),

Preparation 13

The following compounds were prepared in a similar manner to that of Preparation 12.

(1) 3-Allyl-2-indolecarbaldehyde mp : 41°–43° C.

IR (Nujol) : 3300, 1640, 1570, 1530 cm$^{-1}$,

NMR (DMSO-d$_6$, δ) : 3.8–4.0 (2H, m), 4.9–5.2 (2H, m), 5.9–6.2 (1H, m), 7.0–7.1 (1H, m), 7.2–7.5 (2H, m), 7.73 (1H, d, J=8.1Hz), 10.07 (1H, s), 11.73 (1H, s), (2) 3-Ethyl-2-indolecarbaldehyde mp : 64°–67° C.

IR (Nujol) : 3300, 1640, 1610 cm$^{-1}$.

NMR (DMSO-d$_6$, δ) : 1.30 (3H, t, J=7.4Hz), 3.11 (2H, q, J=7.4Hz), 7.0–7.2 (1H, m), 7.3–7.4 (1H, m), 7.44 (1H, d, J=8.08Hz), 7.75 (1H, d, J=8.08Hz), 10.07 (1H, s), 11.64 (1H, s).

(3) 3-Benzyl-2-indolecarbaldehyde mp : 121°–123° C.

IR (Nujol) : 3280, 1645, 1570 cm$^{-1}$.

NMR (DMSO-d$_6$, δ) : 4.48 (2H, s), 7.0–7.5 (8H, m), 7.68 (1H, d, J=8.10Hz), 10.17 (1H, s), 11.78 (1H, s).

Preparation 14

A mixture of 3-methyl-2-indolecarbaldehyde (7.0 g), ammonium acetate (1.4 g) and nitroethane (10.5 ml) in methanol [35 ml] was refluxed for an hour. After the solvent was removed, the residue was dissolved in ethyl acetate, washed with water and brine, dried over anhydrous magnesium sulfate and evaporated in vacuo. The residue was pulverized with isopropyl ether to give 3-methyl-2-[2-nitro-1-propenyl)indole (4.29 g).

mp : 181°–184° C.

IR (Nujol) : 3420, 1630, 1610 cm$^{-1}$.

NMR (DMSO-d$_6$, δ: 2.40 (3H, s), 2.57 (3H, s), 7.1–7.4 (2H, m), 7.49 (1H, d, J=8.22Hz), 7.61 (1H, d, J=7.96Hz), 8.16 (1H, s), 10.97 (1H, s).

Preparation 15

To a solution of 3-ethyl-2-indolecarbaldehyde (4.0 g) and nitromethane (4.93 g) in methanol (80 ml) was added dropwise 50% aqueous sodium hydroxide solution at 0 ~ −5° C. for an hour. After being stirred at the same temperature for an hour and at room temperature an hour. The mixture was poured into a mixture of chilled water and 12N hydrochloric acid (4:1, 500 ml). The precipitates were collected, washed with water and dried to give 3-ethyl-2-(2-nitrovinyl)indole.

mp : 132°–134° C.

IR (Nujol) : 3320, 1630, 1610, 1520 cm$^{-1}$.

NMR (DMSO-d$_6$, δ) : 1.23 (3H, t, J=7.6Hz), 2.95 (2H, q, J=7.6Hz), 7.0–7.1 (1H, m), 7.2–7.5 (2H, m), 7.71 (1H, d, J=8.0Hz), 8.02 (1H, d, J=13.2Hz), 8.14 (1H, d, J=13.2Hz), 11.51 (1H, s).

Preparation 16

A mixture of 3-benzyl-2-indolecarbaldehyde (7.06 g), ammonium acetate (462 mg) and nitromethane (10.5 ml) in methanol (30 ml) was refluxed for 2 hours. After cooling, precipitates formed were collected and washed two times with chilled methanol (5 ml) to give 3-benzyl-2-(2-nitrovinyl)indole.

mp : 171°–174° C.

IR (Nujol) : 1630, 1610 cm$^{-1}$.

NMR (DMSO-d$_6$, δ) : 4.33 (2H, s), 6.9–7.3 (7H, m), 7.41 (1H, d, J=8.24Hz), 7.59 (1H, d, J=8.02Hz), 8.06 (1H, d, J=13.26Hz), 8.26 (1H, d, J=13.26Hz), 11.64 (1H, s)

MS (m/e) : 278 (M$^+$).

Preparation 17

The following compound was prepared in a similar manner to that of Preparation 15.

3-Isopropyl-2-(2-nitrovinyl)indole mp : 190°–193° C.

IR (Nujol) : 3320, 1660, 1520 cm$^{-1}$.

NMR (DMSO-d$_6$, δ) : 1.43 (6H, t, J=7.0Hz), 3.4–3.6 (1H, m), 7.0–7.1 (1H, m), 7.2–7.4 (1H, m), 7.29 (1H, d, J=8.18Hz), 7.80 (1H, d, J=8.18Hz), 8.02 (1H, d, J=13.1Hz), 8.20 (1H, d, J=13.18Hz), 11.49 (1H, s).

Preparation 18

The following compound was prepared in a similar manner to that of Preparation 16.

3-Allyl-2-(2-nitrovinyl)indole mp : 146°–149° C.

IR (Nujol) : 3300, 1605 cm$^{-1}$.

NMR (DMSO-d$_6$, δ) : 3.73 (2H, d, J=6.16Hz), 4.9–5.2 (2H, m), 5.8–6.1 (1H, m), 7.0–7.1 (1H, m), 7.1–7.5 (2H, m), 7.65 (1H, d, J=8.04Hz), 8.02 (1H, d, J=13.23Hz), 8.16 (1H, d, J=13.23Hz), 11.59 (1H, s).

Preparation 19

A mixture of 2-(indol-2-yl)-2-methylpropiononitrile (300 mg) and 5% rhodium on alumina powder (500 mg) in 10N-ammonia-methanol was hydrogenated at 50–60 psi for 8 hours. After filtration of the catalyst, the filtrate was evaporated in vacuo to give 2-(indol-2-yl)-2-methylpropylamine (306 mg) as crystals.

mp : 178°–182° C.

IR (Nujol) : 3250, 1580, 1540 cm$^{-1}$.

NMR (CDCl$_3$, δ) : 1.34 (6H, s), 2.1–3.1 (4H, m), 6.24 (1H, s), 7.0–7.6 (4H, m), 9.54 (1H, br s).

Preparation 20

To a solution of 2-(indol-2-yl)-2-methylpropylamine (363.2 mg) in tetrahydrofuran (10 ml) was added 1,1'-carbonyldiimidazole (340 mg) in small portions at room temperature. After stirring for 3 hours, the reaction mixture was evaporated in vacuo. The residue was purified by silica gel column chromatography (3% methanol-chloroform) to give N-[2-(indol-2-yl)-2-methylpropyl]-1-imidazolecarboxamide (395 mg) as crystals.

mp : 133°–136° C.

IR (Nujol) : 3300, 3200, 1720, 1710, 1615 cm$^{-1}$.

NMR (CDCl$_3$, δ) : 1.46 (6H, s), 3.60 (2H, d, J=6.14Hz), 6.29 (1H, d, J=2.11Hz), 6.9-7.6 (7H, m), 8.17 (1H, s), 9.95 (1H, s).

Preparation 21

To a suspension of lithium aluminum hydride (4.38 g) in tetrahydrofuran (30 ml) at 30°-40° C. under nitrogen atmosphere was added 3-allyl-2-(2-nitrovinyl)indole (3.77 g) in tetrahydrofuran (50 ml). After being stirred at room temperature for 2 hours, the mixture was refluxed for 1 hour. After the reaction mixture was treated with ethyl acetate (60 ml) at 15°-30° C., methanol (5 ml) was added thereto at the same temperature. The mixture was treated with saturated aqueous potassium sodium tartrate solution (100 ml). Separated organic layer was washed with brine, dried over anhydrous magnesium sulfate and filtered. 1,1'-Carbonyldiimidazole (2.8 g) was added to the filtrate in small portions. After overnight stirring, the reaction mixture was evaporated in vacuo. The residue was dissolved in ethyl acetate, washed with water twice, dried over anhydrous magnesium sulfate, and evaporated in vacuo. The residue was purified by silica gel column chromatography (5%-methanol-chloroform) to give N-[2-(3-allylindol-2-yl)ethyl]-1-imidazolecarboxamide (2.60 g) as crystals.

mp : 113°-117° C.

IR (Nujol) : 1720, 1690 cm$^{-1}$.

NMR (DMSO-d$_6$, δ): 3.04 (2H, t, J=6.44Hz), 3.43 (2H, d, J=5.97Hz), 3.5-3.7 (2H, m), 4.8-5.1 (2H, m), 5.8-6.1 (1H, m), 6.91 (1H, s), 7.0-7.5 (5H, m), 7.82 (1H, s).

Preparation 22

The following compounds were prepared in a similar manner to that of Preparation 21.

(1) N-[1-Methyl-2-(3-methylindol-2-yl)ethyl]-1-imidazolecarboxamide mp : 114°-118° C.

IR (Nujol) : 3300, 1700, 1655 cm$^{-1}$.

NMR (DMSO-d$_6$) : 1.20 (3H, d, J=6.69Hz), 2.18 (3H, s), 2.8-3.2 (2H, m), 2.37 (1H, br s), 4.1-4.3 (1H, m), 6.6-7.7 (5H, m), 8.2-8.4 (2H, m), 10.7 (1H, s).

(2) N-[2-(3-Ethylindol-2-yl)ethyl]-1-imidazolecarboxamide mp : 67°-73° C.

IR (CHCl$_3$-solution) : 3300, 1720, 1710, 1660 cm$^{-1}$.

NMR (CDCl$_3$, δ): 1.23 (3H, t, J=7.3Hz), 2.69 (2H, q, J=7.3Hz), 3.07 (2H, t, J=6.75Hz), 3.5-3.8 (2H, m), 6.7-8.7 (8H, m).

(3) N-[2-(3-Benzylindol-2-yl)ethyl]-1-imidazolecarboxamide mp : 71°-74° C.

IR (Nujol) : 3350, 1690 cm$^{-1}$.

NMR (CDCl$_3$, δ) : 3.04 (2H, t, J=6.46Hz), 3.55 (2H, t, J=6.46Hz), 4.06 (2H, s), 6.67 (1H, t, J=5.72Hz), 6.9-7.5 (11H, m), 7.19 (1H, s), 8.68 (1H, s).

(4) N-[2-(3-Isopropylindol-2-yl)ethyl]-1-imidazolecarboxamide mp : 59°-63° C.

IR (Nujol) : 3350, 3250, 1705, 1650 cm$^{-1}$.

NMR (DMSO-d$_6$, δ) : 1.29 (6H, d, J=7.02Hz), 2.98 (2H, t, J=6.92Hz), 3.0-3.2 (1H, m), 3.4-3.6 (2H, m), 6.8-7.0 (3H, m), 7.26 (1H, d, J=7.56Hz), 7.55 (1H, d, J=7.56Hz), 7.60 (1H, s), 8.23 (1H, s), 8.65 (1H, t, J=5.49Hz), 10.75 (1H, s).

(5) N-[2-(3-Phenylindol-2-yl)ethyl]-1-imidazolecarboxamide mp : 85°-80° C.

IR (Nujol) : 1700 cm$^{-1}$.

Preparation 23

To a solution of 2-(indol-2-yl)ethylamine (2.7 g) in acetic acid (25 ml) at 15° C. was added sodium cyanoborohydride (2.22 g) in one portion. The solution was stirred at room temperature for 15 hours and diluted with chilled water. The mixture was made basic with sodium hydroxide pellets and extracted three times with ether. The ether layer was washed with brine, dried over anhydrous magnesium sulfate, and evaporated in vacuo to give 2-(2,3-dihydroindol-2-yl)ethylamine (1.41 g) as an oil. The oil was dissolved in tetrahydrofuran (50 ml) and treated with 1,1'-carboxyldiimidazole (1.13 g) at room temperature. The mixture was stirred at room temperature for 30 minutes. The reaction mixture was washed with brine, dried over anhydrous magnesium sulfate, and evaporated in vacuo. The residue was purified by silica gel column chromatography (30%-ethyl acetate-chloroform) to give crystals. The crystals were washed with ether to give 3,4,4a,5-tetrahydropyrimido[1,6-a]indol-1(2H)-one (0.74 g).

mp : 195°-196° C.

IR (Nujol) : 3320, 1650, 1600.

NMR (DMSO-d$_6$δ) : 1.6-1.9 (1H, m), 2.20 (1H, dd, J=2.95, 12.37Hz), 2.85 (1H, dd, J=10.70, 15.65Hz), 3.1-3.3 (3H, m), 4.1-4.3 (1H, m), 6.68 (1H, s), 6.7-6.9 (1H, m), 7.09 (2H, dd, J=7.85, 17.38Hz), 0.72 (1H, d, J=7.85Hz)

MS (m/e) : 188 (M+).

Preparation 24

A solution of N-[2-(3-ethylindol-2yl)ethyl]-1-imidazolecarboxamide (2.2 g) in toluene (50 ml) was refluxed for 3 hours. After the mixture was evaporated in vacuo, the residue was purified by silica gel column chromatography (5% methanol-chloroform) to give 5-ethyl-3,4-dihydropyrimido[1,6-a]indol-1(2H)-one (0.15 g).

mp : 129°-131° C.

IR (Nujol) : 1700, 1620 cm$^{-1}$.

NMR (DMSO-d$_6$, δ) : 1.17 (3H, t, J=7.41Hz), 2.65 (2H, q, J=7.41Hz), 2.98 (2H, t, J=6.17Hz), 3.35 (2H, t, J=6.17Hz), 7.1-7.6 (3H, m), 7.79 (1H, s), 8.1-8.3 (1H, m).

Preparation 25

A solution of N-[2-(3-benzylindol-2-yl)ethyl]-1-imidazolecarboxamide (2.4 g) in xylene (50 ml) was refluxed for 3 hours. After cooling, the mixture was washed with water and brine, dried over anhydrous magnesium sulfate, and evaporated in vacuo. The residue was purified by silica gel column chromatography (5%-methanol-chloroform) to give a crystalline product. The product was pulverized with n-hexane to give 5-benzyl-3,4-dihydropyrimido[1,6-a]indol-1(2H)-one (1.2 g).

mp : 174°-177° C.

IR (Nujol) : 3200, 1690, 1630 cm$^{-1}$.

NMR (DMSO-d$_6$, δ) : 3.06 (2H, t, J=6.20Hz), 3.39 (2H, t, J=6.20Hz), 4.00 (2H, s), 7.0-7.3 (7H, m), 7.39 (1H, dd, J=0.79Hz), 6.40Hz), 7.86 (1H, s), 8.19 (1H, d, J=7.54Hz)

MS (m/e) : 276 (M+).

Preparation 26

A mixture of N-[2-(3-isopropylindol-2-yl)ethyl]-1-imidazolecarboxamide (2.0 g), 1,8-diazabicyclo[5.4.0]-undec-7-ene (1 g) and toluene (100 ml) was reflux for 1 hour. After cooling, the mixture was washed with water and brine, dried over anhydrous magnesium sulfate, and evaporated in vacuo. The residue was purified by silica gel column chromatography (5% methanol-chloroform) to give 3,4-dihydro-5-isopropyl-pyrimido[1,6-a]indol-1(2H)-one (0.52 g).

mp : 121°-123° C.

IR (Nujol) : 3200, 1695, 1610 cm$^{-1}$.

NMR (CDCl$_3$, δ) : 1.40 (6H, d, J=7.07Hz), 3.0–3.3 (3H, m), 3.4–3.6 (2H, m), 6.04 (1H, s), 7.1–7.3 (2H, m), 7.5–7.7 (1H, m), 8.36 (1H, dd, J=1.45Hz, 6.45Hz).

Preparation 27

The following compounds were prepared in a similar manner to that of Preparation 24.

(1) 3,4-Dihydro-3,5-dimethylpyrimido[1,6-a]indol-1(2H)-one mp : 146°-149° C.

IR (Nujol) : 3200, 1695, 1620 cm$^{-1}$.

NMR (CDCl$_3$, δ): 1.35 (3H, d, J=6.38Hz), 2.19 (3H, s), 2.6–3.3 (2H, m), 3.7–3.9 (1H, m), 5.49 (1H, br s), 7.0–7.6 (3H, m), 8.2–8.4 (1H, m)

MS [m/e] : 214 (M )

(2) 3,4-Dihydro-5-phenylpyrimido[1,6-a]indol-1(2H)-one mp 237°-240° C.

IR (Nujol) : 3200, 3100, 1705, 1605 cm$^{-1}$.

NMR (DMSO$_6$, δ) : 3.12 (2H, t, J=6.10Hz), 3.3–3.5 (2H, m), 7.1–7.7 (8H, m), 8.31 (1H, J=7.39Hz), 7.99 (1H, s).

Preparation 28

The following compounds were prepared in a similar manner to that of Preparation 25.

(1) 3,4-Dihydro-4,4-dimethylpyrimido[1,6-a]indol-1(2H)-one mp : 144°-147° C.

IR (Nujol) : 3250, 1700, 1590 cm$^{-1}$.

NMR (CDCl$_6$, δ): 1.47 (6H, s), 3.27 (2H, d, J=2.81Hz), 5.68 (1H, s), 6.33 (1H, s), 7.1–7.6 (3H, m), 8.36 (1H, d, J=7.76Hz)

MS (m/e) : 214 (M$^+$).

(2) 5-(Allyl-3,4-dihydropyrimido[1,6-a]indol-1(2H)-one mp : 144°-145° C.

IR (Nujol) : 3200, 1700, 1615 cm$^{-1}$.

NMR (DMSO-d$_6$, δ) : 2.98 (2H, t, J=6.29Hz), 3.3–3.5 (4H, m), 4.9–5.2 (2H, m), 5.8–6.1 (1H, m), 7.1–7.3 (2H, m), 7.4–7.6 (1H, m), 7.84 (1H, s), 8.1–8.3 (1H, m)

Preparation 29

To a solution of 1,1,1,3,3,3-hexamethyldisilazane (7.10 g) in tetrahydrofuran (30 ml) at 0° C. under a nitrogen atmosphere was added 1.56 M butyllithium in hexane (28.2 ml). The solution was stirred at room temperature for 15 minutes and then at 0° C. for 20 minutes. The solution of lithium bis(trimethylsilyl)amine prepared above was added to a solution of 5-methyl-1-trityl-1H-imidazole-4-carbaldehyde (14.1 g) in tetrahydrofuran (140 ml) at −70° C. under a nitrogen atmosphere over 8 minutes. After 25 minutes at −70° C., 1.05 M methyllithium in ether (52 ml) was added to the mixture over 8 minutes at the same temperature. The mixture was stirred at −70° C. for 2 hours and 20 minutes, diluted with water, and extracted twice with ether. The combined extracts were washed with water and brine, dried over sodium sulfate, and evaporated in vacuo. The residual oil was chromatographed over silica gel (eluted with 20% methanol in chloroform) to give 4-(1-aminoethyl)-5-methyl-1-trityl-1H-imidazole (9.7 g) as crystals.

mp : 150°-152° C.

IR (Film) : 3300, 1590, 1485, 1440 cm$^{-1}$.

NMR (DMSO-d$_6$, δ) : 1.24 (3H, d, J=6.6Hz), 1.37 (3H, s), 3.15 (2H, br s), 3.86 (1H, q, J=6.6Hz), 7.05–7.78 (16H, m).

Preparation 30

To a solution of lithium diisopropylamide prepared from diisopropylamine (1.11 g) and n-butyllithium (1.61 M in hexane; 7.0 ml), in dry tetrahydrofuran under nitrogen atmosphere at −70° C. was added dropwise over 20 minutes a solution of 3-methyl-1-phenylsulfonylindole (2.71 g) in tetrahydrofuran (20 ml). The mixture was stirred for 1 hour below −70° C. and then allowed to warm slowly to 0° C. over 1 hour. The resulting solution was cooled to −70° C. and then treated with ethylene oxide (484 mg) in dry tetrahydrofuran (5 ml). The mixture was stirred for 1 hour below −70° C. and then allowed to warm slowly to room temperature over 3 hours. After stirring overnight, the reaction mixture was treated with cold water and extracted twice with ethyl acetate. The combined extracts were washed with brine, dried over magnesium sulfate, and evaporated in vacuo. The residue was chromatographed over silica gel (eluted with 5% ethyl acetate in toluene) to give 2-[3-methyl-1-(phenylsulfonyl)indol-2-yl]ethanol (1.19 g).

IR (Film) : 3300, 1450, 1360, 1230, 1170 cm$^{-1}$.

NMR (CDCl$_3$, δ) : 2.19 (3H, s), 1.76 (1H, br s), 3.27 (2H, t, J=6.44Hz), 3.94 (2H, m), 7.1–7.5 (6H, m), 7.6–7.7 (2H, m), 8.1–8.2 (1H, m).

Preparation 31

A mixture of chromium trioxide (1.2 g) and pyridine (1.9 g) in dichloromethane was stirred at ambient temperature for 15 minutes, and then 2-[3-methyl-1-(phenylsulfonyl)indol-2-yl]ethanol (630 mg) in dichloromethane (2 ml) was added. The resultant mixture was stirred at room temperature for 15 minutes. The separated organic layer was washed with water and brine, dried over anhydrous magnesium sulfate, and evaporated in vacuo. The residue was chromatographed over silica gel (eluted with 5% ethyl acetate in toluene) to give 3-methyl-1-(phenylsulfonyl)-2-indole acetaldehyde (423 mg).

mp : 81°-84° C.

IR (Film) : 1725, 1670, 1450 cm$^{-1}$.

NMR (CDCl$_3$, δ) : 2.16 (3H, s), 4.10 (2H, s), 7.1–8.1 (4H, m), 9.77 (1H, s).

Preparation 32

A mixture of 4-(1-aminoethyl)-5-methyl-1-trityl-1H-imidazole (735 mg), 3-methyl-1-(phenylsulfonyl)-2-indoleacetaldehyde (626 mg) and molecular sieves 3A (100 mg) in dry methanol (30 ml) was stirred at ambient temperature for 30 minutes. Acetic acid (0.35 ml) and sodium cyanoborohydride (126 mg) were added and the resulting mixture was stirred at room temperature for 2 hours. The reaction mixture was treated with cold water, extracted twice with ethyl acetate, which was washed with brine and dried over anhydrous magnesium sulfate. After evaporation of the solvent, the residue was chromatographed over silica gel (eluted with 3% methanol in chloroform) to give 3-methyl-2-[2-[[1-(5-methyl-1-trityl-1H-imidazol-4-yl)ethyl]amino]ethyl]-1-phenylsulfonylindole (947 mg) as an amorphous powder.

IR (Nujol) : 1630, 1590, 1230 cm$^{-1}$.

NMR (CDCl$_3$δ) : 1.42 (3H, s), 1.61 (3H, d, J=6.70Hz), 2.18 (3H, s), 2.9-3.1 (2H, m), 3.2-3.5 (2H, m), 4.11 (1H, q, J=6.70Hz), 0-7.8 (24H, m), 8.1-8.2 (1H, m).

Preparation 33

A mixture of 3-methyl-2-[2-[[1-(5-methyl-1-trityl-1H-imidazol-4-yl)ethyl]amino]ethyl]-1-phenylsulfonylindole (970 mg) and powdered potassium hydroxide (819 mg) in dimethylsulfoxide (10 ml) were stirred at 70° C. for 1 hour. The resultant mixture was diluted with cold water and extracted twice with 30% tetrahydrofuran in ethyl acetate. The extracts were washed with brine, dried over anhydrous magnesium sulfate and evaporated in vacuo. The residue was chromatographed on silica gel (eluted with 5% MeOH in chloroform) to give 3-methyl-2-[2-[[1-(5-methyl-1-trityl-1H-imidazol-4-yl)ethyl]amino]ethyl]indole (611.3 mg) as amorphous powder.

IR (Nujol) : 2940, 1460, 1370, 1230 cm$^{-1}$.

NMR (DMS 6) : 1.2-1.4 (6H, m), 2.12 (3H, s), 2.4-2.8 (4H, m), 3.4 (2H, br s), 3.77 (1H, q, J=6.7Hz), 6.8-7.4 (20H, m)

EXAMPLE 1

To a solution of 3,4-dihydro-5-methylpyrimido[1,6-a]indol-1(2H)-one (0.67 g) in N,N-dimethylformamide (8 ml) at 5° C. was added sodium hydride (60% in mineral oil, 0.16 g). The mixture was stirred at 5° C. for 40 minutes and then at room temperature for 15 minutes and again cooled to 5° C. 4-Chloromethyl-5-methyl-1-trityl-1H-imidazole (1.50 g) was added to the solution in small portions over two minutes. After being stirred at 5° C. for 2 hours, the reaction mixture was diluted with chilled water to give precipitates. The precipitates collected were dissolved in dichloromethane. The organic layer was washed with water and brine, dried over anhydrous magnesium sulfate, and evaporated in vacuo. Column chromatography (silica, gel, 0.5% methanol in chloroform as an eluent) of the residue, followed by recrystallization from toluene-hexane, gave 3,4-dihydro-5-methyl-2-[(5-methyl-1-trityl-1H-imidazol-4-yl)methyl]pyrimido[1,6-a]indol-1(2H)-one (1.16 g).

mp : 210°-220° C.

IR (Nujol) : 1680, 1620, 1330 cm$^{-1}$.

NMR (CDCl$_3$, δ) : 1.52 (3H, s), 2.17 (3H, s), 2.94 (2H, t, J=6Hz), 3.64 (2H, t, J=6Hz), 4.67 (2H, s), 7.10-7.52 (19H, m), 8.33 (1H, d, J=6.5Hz).

EXAMPLE 2

A solution of 3,4-dihydro-5-methyl-2-[(5-methyl-1-trityl-1H-imidazol-4-yl)methyl]pyrimido[1,6-a]indol-1(2H)-one (0.9 g) in a mixture of acetic acid and water (4:1, 30 ml) was heated at 65° C. for 3.5 hours. After evaporation of the solvent, the residue was neutralized with aqueous sodium bicarbonate solution and extracted three times with chloroform. The chloroform layer was washed with water and brine, dried over anhydrous magnesium sulfate, and evaporated in vacuo. The residue was purified by silica gel column chromatography (5% methanol-chloroform) to give 3,4-dihydro-5-methyl-2-[(5-methyl-1H-imidazol-4-yl)-methyl]-pyrimido[1,6-a]indol-1(2H)-one (0.447 g) as a powder. This powder was dissolved in a mixture of methanol (40 ml) and 12N hydrochloric acid (0.3 ml). The solution was evaporated to 4 ml and then diluted with ether. The solution was allowed to stand at room temperature to give 3,4-dihydro-5-methyl-2-[(5-methyl-1H-imidazol-4-yl)methyl]pyrimido[1,6-a]indol-1(2H)-one hydrochloride (387 mg).

mp : >250° C.

(Nujol) : 1685, 1630, 1345 cm$^{-1}$.

NMR (DMSO-d$_6$, δ) : 2.15 (3H, s), 2.37 (3H, s), 3.06 (2H, t, J=6Hz), 3.63 (2H, t, J=6Hz), 4.72 (2H, s), 7.22 (2H, m), 7.47 (1H, m), 8.19 (1H, m), 9.00 (1H, s).

EXAMPLE 3

The following compounds were prepared in a similar manner to that of Example 1.

(1) 3,4-Dihydro-2-[(5-methyl-1-trityl-1H-imidazol-4-yl)-methyl]pyrimido[1,6-a]indol-1(2H)-one mp : 128°-131° C.

IR (Nujol) : 1680, 1595 cm$^{-1}$.

NMR (CDCl$_3$, δ) : 1.55 (3H, s), 3.02 (2H, t, J=6.2Hz) 3.66 (2H, t, J=6.2Hz), 4.66 (2H, s), 6.23 (1H, s), 7.0-7.6 (19H, m), 8.32 (1H, d, J=8Hz)

MS (m/e) : 522 (M+).

(2) 3,4,4a,5-Tetrahydro-5-methyl-2-[(5-methyl-1-trityl-1H-imidazol-4-yl)methyl]pyrimido[1,6-a]indol-1(2H)-one IR (Nujol) : 1635, 1595, 1295, 1220 cm$^{-1}$.

NMR (DMSO-d$_6$, δ) : 1.32 (3H, d, J=6.5Hz), 1.39 (3H, s), 1.76 (1H, m), 2.30 (1H, m), 3.12 (1H, m), 3.20-3.40 (2H, m), 3.70 (1H, dt, J=3, 10Hz), 4.40 (2H, dd, J=14, 20Hz), 6.84-7.50 (19H, m), 7.75 (1H, d, J=8Hz).

(3) 3,4,4a,5-Tetrahydro-2-[(5-methyl-1-trityl-1H-imidazol-4-yl)methyl]pyrimido[1,6-a]indol-1(2H)-one mp : 213°-217° C. (dec.)

IR (Nujol) : 1640, 1630, 1590 cm$^{-1}$.

NMR (DMSO-d$_6$, δ) : 1.39 (3H, s), 1.7-1.9 (1H, m), 2.2-2.3 (1H, m), 2.7-2.9 (1H, m), 3.2-3.4 (3H, m), 4.1-4.3 (1H, m), 4.40 (2H, s), 6.83 (1H, t, J=7.02Hz), 7.0-7.5 (18H, m), 7.75 (1H, d, J=7.93Hz).

MS (m/e) : 524 (M+).

(4) 3,4-Dihydro-3,5-dimethyl-2-[(5-methyl-1-trityl-1H-imidazol-4-yl)methyl]pyrimido[1,6-a]indol-1(2H)-one mp : 94°-108° C. .

IR (Nujol) : 1680, 1620 cm$^{-1}$.

NMR (DMSO-d$_6$, δ) : 0.99 (3H, d, J=6.48Hz), 1.43 (3H, s), 2.16 (3H, s), 2.7-3.2 (2H, m), 3.7-3.9 (1H, m), 4.38, 4.85 (2H, ABq, J=14.8Hz), 6.9-7.5 (19H, m), 8.1-8.2 (1H, m).

MS (m/e) : 550 (M+).

EXAMPLE 4

The following compounds were prepared in a similar manner to that of the former half of Example 2.

(1) 3,4-Dihydro-2-[(5-methyl-1H-imidazol-4-yl)methyl]-pyrimido[1,6-a]indol-1(2H)-one mp : 228°-230° C.

IR (Nujol) : 1785, 1590 cm$^{-1}$.

NMR (CDCl$_3$+CD$_3$OD, 6) : 2.29 (3H, s), 3.04 (2H, t, J=6.28Hz), 3.55 (2H, t, J=6.28Hz), 3.9 (1H, br s), 4.62 (2H, s), 6.25 (1H, s), 7.1-7.3 (2H, m), 7.44 (1H, s), 7.4-7.5 (1H, m), 8.31 (1H, d, J=8.64Hz).

MS (m/e) : 280 (M+).

(2) 3,4,4a,5-Tetrahydro-2-[(5-methyl-1H-imidazol-4-yl)-methyl]pyrimido[1,6-a]indol-1(2H)-one mp : 225°–227° C.

IR (Nujol) : 1640, 1595 cm$^{-1}$.

NMR (DMSO-d$_6$, δ) : 1.6–2.3 (2H, m), 2.17 (3H, s), 2.4–3.4 (4H, m), 4.1–4.3 (1H, m), 4.39 (2H, m), 6.7–6.9 (1H, m), 7.0–7.2 (2H, m), 7.41 (1H, s), 7.79 (1H, d, J=7.81Hz), 11.71 (1H, br s).

MS (m/e) : 282 (M$^+$).

EXAMPLE 5

The following compounds were prepared in a similar manner to that of Example 2.

(1) 3,4,4a,5-Tetrahydro-5-methyl-2-[(5-methyl-1H-imidazol-4-yl)methyl]pyrimido[1,6-a]indol-(2H)-one hydrochloride mp : >255° C. .

IR (Nujol) : 2740, 2640, 1645, 1595, 1300 cm$^{-1}$.

NMR (DMSO-d$_6$, δ) : 1.32 (3H, d, J=7Hz), 1.95 (1H, m), 2.30 (1H, m), 2.32 (3H, s), 3.13 (1H, m), 3.40 (2H, m), 3.78 (1H, dd, J=2, 11Hz), 4.57 (2H, dd, J=15, 18Hz), 6.91 (1H, t, J=7Hz), 7.15 (2H, m), 7.77 (1H, d, J=7Hz), 8.96 (1H, s)

(2) 3,4-Dihydro-3,5-dimethyl-2-[(5-methyl-1H-imidazol-4-yl)methyl]pyrimido[1,6-a]indol-1(2H)-one hydrochloride mp : 262°–264° C. (dec.).

IR (Nujol) : 1675, 1625 cm$^{-1}$.

NMR (DMSO-d$_6$δ) : 1.07 (3H, d, J=6.50Hz), 2.16 (3H, s), 2.37 (3H, s), 2.9–3.2 (2H, m), 4.0–4.1 (1H, m), 4.06, 4.98 (2H., ABq, J=15.70Hz), 7.1–7.3 (2H, m), 7.4–7.5 (1H, m), 8.1–8.2 (1H, m), 9.00 (1H, s), 14.62 (1H, br s).

MS (m/e) : 308 (M$^+$).

EXAMPLE 6

The following compound was prepared in similar manners to those of Example 1 and the former half of Example 2, successively.

5-Benzyl-3,4-dihydro-2-[(5-methyl-1H-imidazol-4-yl)-methyl]pyrimido[1,6-a]indol-1(2H)-one mp : 241°–245° C.

IR (Nujol) : 1685, 1610 cm$^{-1}$.

NMR (DMSO-d$_6$, δ) : 2.21 (3H, s), 3.06 (2H, t, J=6.27Hz), 3.54 (2H, t, J=6.27Hz), 3.98 (2H, s), 4.55 (2H, s), 7.0–7.3 (7H, m), 7.40 (1H, d, J=6.63Hz), 7.45 (1H, s), 8.21 (1H, d, J=7.51Hz), 11.8 (1H, br s).

MS (m/e) : 370 (M$^+$).

EXAMPLE 7

The following compounds were prepared in similar manners to those of Example 1 and Example 2, successively.

(1) 3,4-Dihydro-4,4-dimethyl-2-[(5-methyl-1H-imidazol-4-yl)methyl]pyrimido[1,6-a]indol-1(2H)-one hydrochloride mp : 255°–262° C. (dec.).

IR (Nujol) 1685, 1635 cm$^{-1}$.

NMR (DMSO-d$_6$, δ) : 1.28 (6H, s), 2.39 (3H, s), 3.45 (2H, s), 4.76 (2H, s), 6.44 (1H, s), 7.1–7.6 (3H, m), 8.24 (1H, d, J=7.1Hz), 9.01 (1H, s), 14.7 (1H, br s).

MS (m/e) : 308 (M$^+$).

(2) 5-Isopropyl-3,4-dihydro-2-[(5-methyl-1H-imidazol-4-yl)methyl]pyrimido[1,6-a]indol-1(2H)-one hydrochloride mp : 258°–260° C. (dec.)

IR (Nujol) : 3090, 1690, 1630, 1615 cm$^{-1}$.

NMR (DMSO-d$_6$, δ) : 1.33 (6H, d, J=7.01Hz), 2.38 (3H, s), 3.0–3.2 (3H, m), 3.65 (2H, t, J=6.21Hz), 4.73 (2H, s), 7.1–7.3 (2H, m), 7.6–7.7 (1H, m), 8.2–8.3 (1H, m), 9.02 (1H, s), 14.76 (2H, br s)

MS (m/e) : 322 (M$^+$).

(3) 5-Allyl-3,4-dihydro-2-[(5-methyl-1H-imidazol-4-yl)-methyl]pyrimido[1,6-a]indol-1(2H)-one hydrochloride mp : 192°–194° C.

IR (Nujol) : 1690, 1630 cm$^{-1}$.

NMR (DMSO-d$_6$, δ) : 2.37 (3H, s), 3.07 (2H, t, J=6.17Hz), 3.40 (2H, d, J=6.17Hz), 4.72 (2H, s), 5.0–5.2 (2H, m), 5.8–6.1 (1H, m), 7.1–7.3 (2H, m), 7.4–7.6 (1H, m), 8.1–8.3 (1H, m), 9.01 (1H, s), 14.7 (1H, br s).

(4) 3,4-Dihydro-5-methyl-2-[(1H-imidazol-4-yl)methyl]-pyrimido[1,6-a]indol-1(2H)-one hydrochloride mp : 266°–269° C.

IR (Nujol) : 3450, 1680, 1610 cm$^{-1}$.

NMR (DMSO-d$_6$, δ) : 2.16 (3H, s), 3.09 (2H, t, J=6.12Hz), 3.63 (2H, t, J=6.12Hz), 4.77 (2H, s), 7.1–7.3 (2H, m), 7.4–7.5 (1H, m), 7.68 (1H, s), 8.1–8.3 (1H, m), 9.09 (1H, d, J=1.26Hz)

MS (m/e) : 280 (M$^+$).

(5) 5-Ethyl-3,4-dihydro-2-[(5-methyl-1H-imidazol-4-yl-methyl]pyrimido[1,6-a]indol-1(2H)-one hydrochloride mp : 264°–266° C. (dec.).

IR (Nujol) : 3110, 2750, 2650, 1693, 1630 cm$^{-1}$.

NMR (DMSO-d$_6$, δ) : 1.16 (3H, t, J=7.4Hz), 2.37 (3H, s), 2.64 (2H, q, J=7.4Hz), 3.07 (2H, t, J=6.3Hz), 3.63 (2H, t, J=6.3Hz), 4.72 (2H, s), 7.1–7.3 (2H, m), 7.4–7.6 (1H, m), 8.1–8.3 (1H, m), 9.00 (1H, s), 14.6 (1H, br s)

MS (m/e) : 308 (M$^+$).

(6) 3,4-Dihydro-2-[(5-methyl-1H-imidazol-4-yl)methyl]-5-phenylpyrimido[1,6-a]indol-1(2H)-one hydrochloride mp : 257°–260° C. (dec.).

IR (Nujol) : 3300, 1675, 1540 cm$^{-1}$.

NMR (DMSO-d$_6$, δ) : 2.39 (3H, s), 3.21 (2H, t, J=6.0Hz), 3.67 (2H, t, J=6.0Hz), 4.77 (2H, s), 7.2–7.7 (8H, m), 8.34 (1H, d, J=7.16Hz), 9.03 (1H, s), 14.7 (1H, br s).

MS (m/e) : 356 (M$^+$).

(7) 2-[(5-Ethyl-1H-imidazol-4-yl)methyl]-3,4-dihydro-5-methylpyrimido[1,6-a]indol-1(2H)-one hydrochloride mp : 241°–244° C. (dec.).

IR (Nujol) : 1680, 1600 cm$^{-1}$.

NMR (DMSO-d$_6$, δ) : 1.22 (3H, t, J=7.4Hz), 2.15 (3H, s), 2.79 (2H, q, J=7.4Hz), 3.06 (2H, t, J=7.54Hz), 3.63 (2H, t, J=7.54Hz), 4.74 (2H, s), 7.1–7.3 (2H, m), 7.4–7.5 (1H, m), 8.1–8.3 (1H, m), 9.05 (1H, s), 14.7 (1H, s).

MS (m/e) : 308 (M$^+$).

EXAMPLE 8

To a solution of 3,4-dihydro-5-methylpyrimido[1,6-a]indol-1(2H)-one (1.88 g) in N,N-dimethylformamide (30 ml) was added sodium hydride (60% in mineral oil 1.12 g) at 5° C. After being stirred at 5° C. for 30 minutes, 4-(2-chloroethyl)-5-methyl-1H-imidazole hydrochloride (2.17 g) in N,N-dimethylformamide (30 ml) was added dropwise over 20 minutes. The mixture was stirred at 5° C. for 30 minutes and at ambient temperature for 16 hours. The reaction mixture was diluted with chilled water and extracted with a mixture of ethyl acetate and tetrahydrofuran (2:1, 30 ml×2). The organic layer was washed with brine, dried over anhydrous magnesium sulfate, and evaporated in vacuo. The residue was purified by silica gel column chromatography (3%-methanol-chloroform) to give 3,4-dihydro-5-methyl-2-[1-(5-methyl-1H-imidazol-4-yl)ethyl]-pyrimido[1,6-a]indol-1(2H)-one as a powder.

mp : 230°-237° C. (dec.)

IR (Nujol) : 1675, 1635, 1625 cm⁻¹.

NMR (DMSO-d6, δ) : 1.51 (3H, d, J=7.08Hz), 2.12 (3H, s), 2.17 (3H, s), 2.8–3.6 (4H, m), 5.75 (1H, , J=7.08Hz), 7.1–7.3 (2H, m), 7.4–7.5 (1H, m), 7.60 (1H, s), 8.1–8.3 (1H, m)

MS (m/e) : 308 (M+).

The powder was dissolved in ethyl acetate and treated with hydrogen chloride in ethanol to give 3,4-dihydro-5-methyl-2-[1-(5-methyl-1H-imidazol-4-yl)-ethyl]-pyrimido[1,6-a]indol-1(2H)-one hydrochloride (72 mg)

IR (Nujol) : 1675, 1640, 1620 cm⁻¹.

EXAMPLE 9

To a solution of 3,4-dihydro-5-methylpyrimido[1,6-a]-indol-1(2H)-one (188 mg) in N,N-dimethylformamide (3 ml) was added sodium hydride (60% in mineral oil, 88 mg) at 5° C. The mixture was stirred at the same temperature for 20 minutes. A solution of 4-chloromethylpyridine hydrochloride in N,N-dimethylformamide (3 ml) was added dropwise at 5° C. over five minutes. The reaction mixture was stirred at the same temperature for 30 minutes and at room temperature for 3 hours. The reaction mixture was diluted with chilled water and extract two times with 5%-methanol-chloroform. The extract was washed twice with water, dried over anhydrous magnesium sulfate, and evaporated in vacuo. The residue was dissolved in 1N-hydrochloric acid (10 ml) and evaporated in vacuo. The residue was pulverized with acetone to give 3,4-dihydro-5-methyl-2-(4-pyridylmethyl)pyrimido[1,6-a]-indol-1(2H)-one hydrochloride (160 mg).

mp : 198°-203° C.

IR (Nujol) : 3170, 1675, 1525 cm⁻¹.

NMR (DMSO-d6, δ) : 2.19 (3H, s), 3.17 (2H, t, J=6.31Hz), 3.69 (2H, t, J=6.31Hz), 4.99 (2H, s), 7.1–7.3 (2H, m), 7.4–7.6 (1H, m), 8.04, 8.87 (4H, ABq, J=6.29Hz), 8.1–8.2 (1H, m)

MS (m/e) : 291 (M+).

EXAMPLE 10

To a solution of 3,4-dihydro-5-methyl-2-[(5-methyl-1H-imidazol-4-yl)methyl]pyrimido[1,6-a]indol-1(2H)-one (343 mg) in N,N-dimethylformamide (20 ml) was added sodium hydride (60% in mineral oil, 51.3 mg) at 5° C. and the mixture was stirred at the same temperature for 30 minutes. Methyl iodide (182 mg) in N,N-dimethylformamide (10 ml) was added dropwise to the solution at 5° C. during 2 hours. After 30 minutes of stirring at the same temperature the reaction mixture wa evaporated in s vacuo. The residue was diluted with a mixture of tetrahydrofuran and ethyl acetate (1:3, 20 ml), washed with brine, dried over anhydrous magnesium sulfate and evaporated in vacuo. The residue was purified by silica gel column chromatography (3%-methanol-chloroform) to give 3,4-dihydro-5-methyl-2-[(1,5-dimethylimidazol-4-yl)-methyl]pyrimido[1,6-a]indol-1(2H)-one as crystal. The crystal was dissolved with 2N-hydrochloric acid (2 ml) and evaporated in vacuo. The crystalline residue was washed with acetone to give 3,4-dihydro-5-methyl-2-[(1,5-dimethylimidazol-4-yl)methyl]pyrimido[1,6-a]indol-1(2H)-one hydrochloride (0.2 g).

mp : 221°-225° C.

IR (Nujol) : 1670, 1625 cm⁻¹.

NMR (DMSO-d6, δ) : 2.13 (3H, s), 2.20 (3H, s), 2.96 (2H, t, J=6.22Hz), 3.50 (3H, s), 3.52 (2H, t, J=6.22Hz), 4.50 (2H, s), 7.1–7.3 (2H, m), 7.4–7.5 (1H, m), 7.47 (1H, s), 8.1–8.3 (1H, m).

MS (m/e) : 308 (M+).

EXAMPLE 11

A mixture of 3-methyl-2-[2-[[1-(5-methyl-1-trityl-1H-imidazol-4-yl)ethyl]amino]ethyl]indole (262 mg), N,N'-carbonyldiimidazole (210 mg), 1.8-diazabicyclo[5.4.0]-7-undecene (84 mg) and molecular sieves (100 mg) in dry tetrahydrofuran (3 ml) was stirred at reflux for 2 hours. The reaction mixture was diluted with ethyl acetate, washed with water and brine, dried over anhydrous magnesium sulfate and evaporated in vacuo. The residue was chromatographed over silica gel (eluted with 5% methanol in chloroform) to give 3,4-dihydro-5-methyl-2-[1-(5-methyl-1-trityl-1H-imidazol-4-yl)ethyl]-pyrimido[1,6-a]indol-1(2H)-one (208 mg) as glassy solid.

mp 71°-76° C.

IR (CHCl3) : 1670, 1620 cm⁻¹.

NMR (DMSO-d6, δ) : 1.39 (3H, s), 1.52 (3H, d, J=7.0Hz), 2.15 (3H, s), 2.5–3.5 (4H, m), 5.68 (1H, q, J=7.0Hz), 7.0–7.5 (18H, m), 8.1–8.2 (1H, m).

EXAMPLE 12

A mixture of 3,4-dihydro-5-methyl-2-[1-(5-methyl-1-trityl-1H-imidazol-4-yl)ethyl]pyrimido[1,6-a]indol-1(2H)-one (60 mg) in 70% acetic acid in water (2.6 ml) was stirred at 60° C. for 2 hours. After evaporation of the solvent, the residue was dissolved in 10% methanol in chloroform. The mixture was washed with aqueous sodium bicarbonate solution and brine, dried over anhydrous magnesium sulfate, and evaporated in vacuo. The residue was purified by silica gel column chromatography (10% methanol-chloroforms) to give 3,4-dihydro-5-methyl-2-[1-(5-methyl-1H-imidazol-4-yl)ethyl]-pyrimido[1,6-a]-indol-1(2H)-one as a powder. The powder was dissolved in 9N hydrogen chloride in ethanol (1 ml) and evaporated in vacuo. The residue was triturated with ether to give 3,4-dihydro-5-methyl-2-[1-(5-methyl-1H-imidazol-4-yl)-ethyl]pyrimido[1,6-a]indol-1(2H)-one hydrochloride (36.8 mg).

mp : 239°-241° C.

IR (Nujol) 1675, 1640, 1630 cm⁻¹.

NMR (DMSO-d6, δ) : 1.66 (3H, d, J=7.24Hz), 2.14 (3H, s), 2.35 (3H, s), 2.9–3.1 (2H, m), 3.3–3.7 (2H, m), 5.82 (1H, q, J=7.24Hz), 7.1–7.3 (2H, m), 7.4–7.5 (1H, m), 8.1–8.2 (1H, m), 9.04 (1H, s), 14.6 (2H, bs).

What we claim is:

1. A compound of the formula:

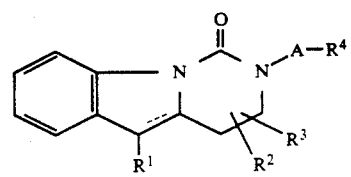

wherein $R^1$, $R^2$, and $R^3$ are each hydrogen, lower alkyl, lower alkenyl, $C_{6-10}$ aryl or $C_{6-10}$ ar(lower)alkyl, $R^4$ is imidazolyl which is 1H-imidazolyl or 1H-imidazolyl having an imino protective group as a substituent in the 1 position, each of which may have lower alkyl as substituent(s), the number of substituents including the imino protective group being 1 to 3, or is pyridyl, A is lower alkylene, and ⋯⋯ is single bond or double bond, and pharmaceutically acceptable salts thereof.

2. A compound of the formula

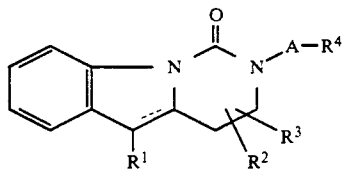

wherein $R^1$, $R^2$ and $R^3$ are each hydrogen, lower alkyl, lower alkenyl, $C_{6-10}$aryl or $C_{6-10}$ar(lower)alkyl, $R^4$ is imidazolyl which is 1H-imidazolyl or 1-$C_{6-10}$ar(lower)alkyl substituted 1H-imidazolyl, each of which may have lower alkyl as substituent(s), the number of substituents including the 1-$C_{6-10}$ar(lower)alkyl group being 1 to 3 or is pyridyl, A is lower alkylene, and ⋯⋯ is single bond or double bond, and pharmaceutically acceptable salts thereof.

3. A compound of claim 2, wherein $R^4$ is 1H-imidazol-4-yl, 5-lower alkyl-1H-imidazol-4-yl, 1-$C_{6-10}$ar(lower)alkyl-5-lower alkyl-1H-imidazol-4-yl, 1-$C_{6}$-ar(lower)alkyl-1H-imidazol-4-yl, 1-lower alkyl-5-lower alkyl-1H-imidazol-4-yl or 4-pyridyl.

4. A compound of claim 3, wherein $R^1$, $R^2$ and $R^3$ are each hydrogen, lower alkyl, lower alkenyl, phenyl or mono- or di- or triphenyl(lower)alkyl, and $R^4$ is 1H-imidazol-4-yl, 5-lower alkyl-1H-imidazol-4-yl, 1- mono- or di- or triphenyl (lower)alkyl-5-lower alkyl-1H-imidazol-4-yl, 1- mono- or di- or triphenyl(lower)alkyl-1H-imidazol-4-yl, 1-lower alkyl-5-lower alkyl-1H-imidazol-4-yl or 4-pyridyl, 5. A compound of claim 4, wherein $R^1$ is lower alkyl, $R^2$ and $R^3$ are each hydrogen, $R^4$ is 5-lower alkyl-1H-imidazol-4-yl, and ⋯⋯ is double bond.

6. A compound of claim 5, which is 3,4-dihydro-5-methyl-2-[1-(5-methyl-1H-imidazol-4-yl)ethyl]-pyrimido[1,6-a]indol-1(2H)-one or its acid addition salt.

7. A pharmaceutical composition comprising a compound of the following formula

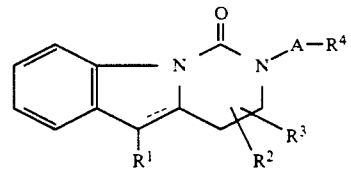

wherein $R^1$, $R^2$ and $R^3$ are each hydrogen, lower alkyl, lower alkenyl, $C_{6-10}$aryl or $C_{6-10}$ar(lower)alkyl, $R^4$ is 1H-imidazolyl which may have 1 to 3 lower alkyl as substituent(s) or is pyridyl, A is lower alkylene, and ⋯⋯ is a single bond or double bond or pharmaceutically acceptable salt thereof in association with a pharmaceutically acceptable, substantially non-toxic carrier or excipient, said compound being present in an amount effective to perform as a 5-HT antagonist.

8. A method for treating or preventing 5-hydroxytryptamine mediated diseases which comprises administering a compound of the following formula

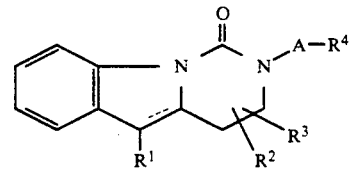

wherein $R^1$, $R^2$ and $R^3$ are each hydrogen, lower alkyl, lower alkenyl, $C_{6-10}$aryl or $C_{6-10}$ar(lower)alkyl, $R^4$ is 1H-imidazolyl which may have 1 to 3 lower alkyl as substituent(s) or is pyridyl, A is lower alkylene, and ⋯⋯ is a single bond or double bond or pharmaceutically acceptable salt thereof in an amount effective to perform as a 5-hydroxytryptamine antagonist to human being or animals in need of such treatment or preventive administration.

9. A method for treating or preventing nausea or vomiting mediated by 5-hydroxytryptamine which comprises administering a compound of the following formula

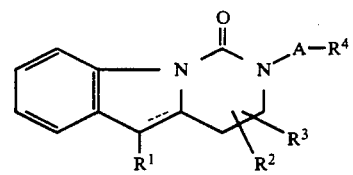

wherein $R^1$, $R^2$ and $R^3$ are each hydrogen, lower alkyl, lower alkenyl, $C_{6-10}$aryl or $C_{6-10}$ar(lower)alkyl, $R^4$ is 1H-imidazolyl which may have 1 to 3 lower alkyl as substituent(s) or is pyridyl, A is lower alkylene, and ⋯⋯ is a single bond or double bond or pharmaceutically acceptable salt thereof in an amount effective to perform as a 5-hydroxytryptamine antagonist to human being or animals in need of such treatment or preventive administration.

* * * * *